United States Patent [19]

Bauman et al.

[11] Patent Number: 4,769,607
[45] Date of Patent: Sep. 6, 1988

[54] CAUSTIC MONITORING AND CONTROL SYSTEM AND PROBE

[75] Inventors: Clarence A. Bauman; Martin P. Step; Alfred J. Gilmour, all of Ontario, Canada

[73] Assignee: Auto-Flush Systems, Ltd., Waterloo, Canada

[21] Appl. No.: 911,130

[22] Filed: Sep. 24, 1986

[51] Int. Cl.[4] .......................................... G01N 27/10
[52] U.S. Cl. .................................... 324/446; 324/439
[58] Field of Search ............... 324/438, 439, 442, 444, 324/446, 448, 449, 450, 65 P; 340/605, 618

[56] References Cited

U.S. PATENT DOCUMENTS

| | | | |
|---|---|---|---|
| 3,714,555 | 1/1973 | Greer | 324/442 |
| 3,996,509 | 12/1976 | Seger | 324/450 |
| 4,205,237 | 5/1980 | Miller | 324/65 P |
| 4,362,994 | 12/1982 | Goldsmith et al. | 324/449 |
| 4,459,584 | 7/1984 | Clarkson | 340/618 |
| 4,518,955 | 5/1985 | Meyer | 340/605 |
| 4,591,837 | 5/1986 | Martinez | 340/605 |

FOREIGN PATENT DOCUMENTS

913181  10/1972  Canada .

Primary Examiner—Reinhard J. Eisenzopf
Assistant Examiner—Anthony L. Miele
Attorney, Agent, or Firm—Paul M. Denk

[57] ABSTRACT

Sensor assembly and system for sensing conductivity and thereby controlling the concentration and level of a solution includes first and second probes adapted to be at least partially immersed in the solution whose conductivity is to be sensed. The probes are fixedly supported in a predetermined geometrical relationship with respect to each other in an externally mounted housing. Each of the first and second probes has an outer insulative sheath and an inner conductive electrode, the electrodes being exposed to the solution at least one point when their probes are immersed therein. At least one of the electrodes is recessed a predetermined distance from an open end of its respective sheath so that the solution must fill a predetermined volume in the sheath corresponding to the predetermined distance before contacting the electrode. The probe including that one of the electrodes has a clear path therethrough to permit solution to rise therein to a level of the electrode. The resistance between the two probes is a function of the conductivity of the solution between the two probes, this solution in the predetermined volume in the one probe providing a substantial portion of the total resistance between the two electrodes. An alternating current waveform is applied across the first and second probes to determine the resistance therebetween.

7 Claims, 6 Drawing Sheets

CAUSTIC MONITORING AND CONTROL SYSTEM AND PROBE

BACKGROUND OF THE INVENTION

This invention relates to process controllers and sensors and more particularly to such controllers and sensors suitable for sensing and controlling the concentration of a caustic solution in bottle washing machinery and a sampling device for use therewith.

In the past there have been numerous attempts to automate the control of caustic soda solution concentrations in commercial bottlewashers. These attempts are believed to have had only limited success. For example, there are believed to be no commercially available systems or devices that can achieve caustic solution concentration control at a satisfactory level of accuracy.

The caustic soda solution in a bottlewasher is typically used at strengths of no less than 3% and no higher than 6%. Such a bottlewasher normally includes a number of tanks containing caustic at differing concentrations followed by one or more tanks containing rinse water, which desirably has little or no caustic therein. Thus, the solution strength in any one compartment of the bottlewasher cannot be allowed to vary over the entire range of from 3 to 6%. On the contrary, each bottlewasher tank has rather narrowly defined limits of solution concentration for that tank. Achieving acceptably clean bottles at a given rate of production within the limits of the specific bottlewasher's capacity, requires a predetermined "soaking time" per bottle at specific caustic strengths and specific temperatures.

Presently, the task of maintaining the correct solution strength for each tank is accomplished by periodically manually drawing samples from each compartment or tank for lab analysis. The commonly accepted method of testing is differential titration. A small, carefully measured volume of the sample solution is placed in a glass flask. Phenolphthalein indicator is added to the glass flask, which turns the solution pink. By means of a burette, acid is slowly added to the mixture in the flask until the pink color just disappears. The number of drops of acid used is recorded and used to calculate the per cent caustic.

The problem with differential titration is that the samples drawn from the bottlewasher are very dirty. In fact they are virtually opaque from all the dirt, dissolved labels and the like from the bottles being washed. This fact makes it very difficult to judge the point of color change in differential titration with any high degree of accuracy. In addition, since this titration process is accomplished manually, there is also the ever present possibility of human error. Even assuming that the caustic concentration is measured accurately by this manual process, present systems are adversely affected by the fact that the necessary changes to solution strengths are then made under manual control using the same large diameter fill line and centrifugal pumps which are used to fill the tanks or compartments at the start of the production line. As a result, the amount of caustic that is added to the tank or compartment cannot be accurately determined. In addition, the strength of what is added is generally in doubt because only a single fill line is commonly used for both high and low strength caustic.

The level of solution in the compartments is usually checked manually as well. This checking is necessary since a certain minimum amount of solution is needed in each tank to ensure that all of the bottles are completely submersed. The entire checking process is tedious, labor intensive, and fraught with hazards from constant handling of the highly corrosive material. The process is also slow, and in fact, problems often develop between sampling intervals which are severe enough to cause operational or product quality problems.

Until the present, it has been difficult to automate this testing for several reasons. For one, previous sensor probe designs were prone to virtually constant contamination with scale build-up, sludge, labels, and dirt. Such probes have been extremely unreliable and have required constant maintenance. In addition, previous probes were incapable of discriminating accurately between solutions that vary only slightly in strength. As a result, such probes could not maintain the solution within a close enough tolerance to a desired level to justify their expense, especially when they needed constant cleaning in order to work at all. At least one probe and system, shown in Canadian Pat. No. 913,181, issued Oct. 24, 1972 has been designed to address some of these problems. However, the accuracy, safeguards, and reliability of this particular probe and system could be improved.

SUMMARY OF THE INVENTION

Among the various objects and features of the present invention may be noted the provision of a caustic monitoring and control system which eliminates the need for constant manual sampling and analysis of caustic solution strength.

Another object of the present invention is the provision of such a system which eliminates the need for manually correcting the caustic solution concentration.

A third object of the present invention is the provision of such a system which controls the caustic concentration more accurately than previous systems.

A fourth object of the present invention is the provision of such a system which adds an accurate amount of caustic to the solution when changes in the concentration are needed.

Another object of the present invention is the provision of such a system which reduces or eliminates the problem of rejected bottles occuring because the bottles are not clean enough or have caustic carryover.

Another object of the present invention is the provision of such a system which detects accurately and quickly the rapid dropping of solution levels and similar problems in bottle washing systems, thereby preventing severe damage to the bottlewasher.

Another object of the present invention is the provision of such a system which makes more efficient use of caustic through the elimination of overflows and the early detection of slow leaks.

Another object of the present invention is the provision of such a system which eliminates the frequent handling of hazardous materials.

Another object of the present invention is the provision of such a system which can maintain accurate records of caustic usage and allocate that usage to the various causes.

Other objects and features will be in part apparent and in part pointed out hereinafter.

Briefly, a sensor assembly of the present invention is particularly adapted for sensing the conductivity of a solution. It includes first and second probes adapted to be partially immersed in the solution whose conductivity is to be sensed. The probes are fixedly supported in a predetermined geometrical relationship with each other. Each of the first and second probes has an outer, insulative sheath and an inner, conductive electrode, the electrodes being exposed to the solution at at least one point when their probes are immersed therein. At least one of the electrodes is recessed a predetermined distance from an open end from its respective sheath so that the solution must fill a predetermined volume in the sheath corresponding to the predetermined distance before contacting the electrode. The probe including that one of the electrodes has a fluid path therethrough to permit solution to rise therein to the level of the electrode. The resistance between the two probes is a function of the conductivity of the solution between the two probes, the solution in the predetermined volume in the one probe providing a substantial portion of the total resistance between the two electrodes.

More specifically, the system of the present invention includes first and second probes adapted to be at least partially immersed in the solution whose conductivity is to be sensed. These probes are fixedly supported in a predetermined geometrical relationship with respect to a compartment in which the solution is disposed, as previously explained. Each of the first and second probes has its outer, insulative sheath and an inner, conductive electrode, the electrodes being exposed to the solution at at least one point when their probes are immersed therein. At least one of the electrodes is recessed a predetermined distance from an open end of its respective sheath so that the solution must fill a predetermined volume in the sheath corresponding to the predetermined distance before contacting the electrode. The probe including that one of the electrodes has a fluid path therethrough to permit solution to rise therein to the level of the electrode. An alternating current waveform is applied across the first and second probes, the resistance between the two probes being a function of the conductivity of the solution between the two probes, the solution in the predetermined volume in the one probe providing a substantial portion of the total resistance between the two electrodes.

BRIEF DESCRIPTION OF THE DRAWINGS

Similar reference characters indicate similar parts throughout the several views of the drawings.

BRIEF DESCRIPTION OF THE PREFERRED EMBODIMENT

Figure 1:
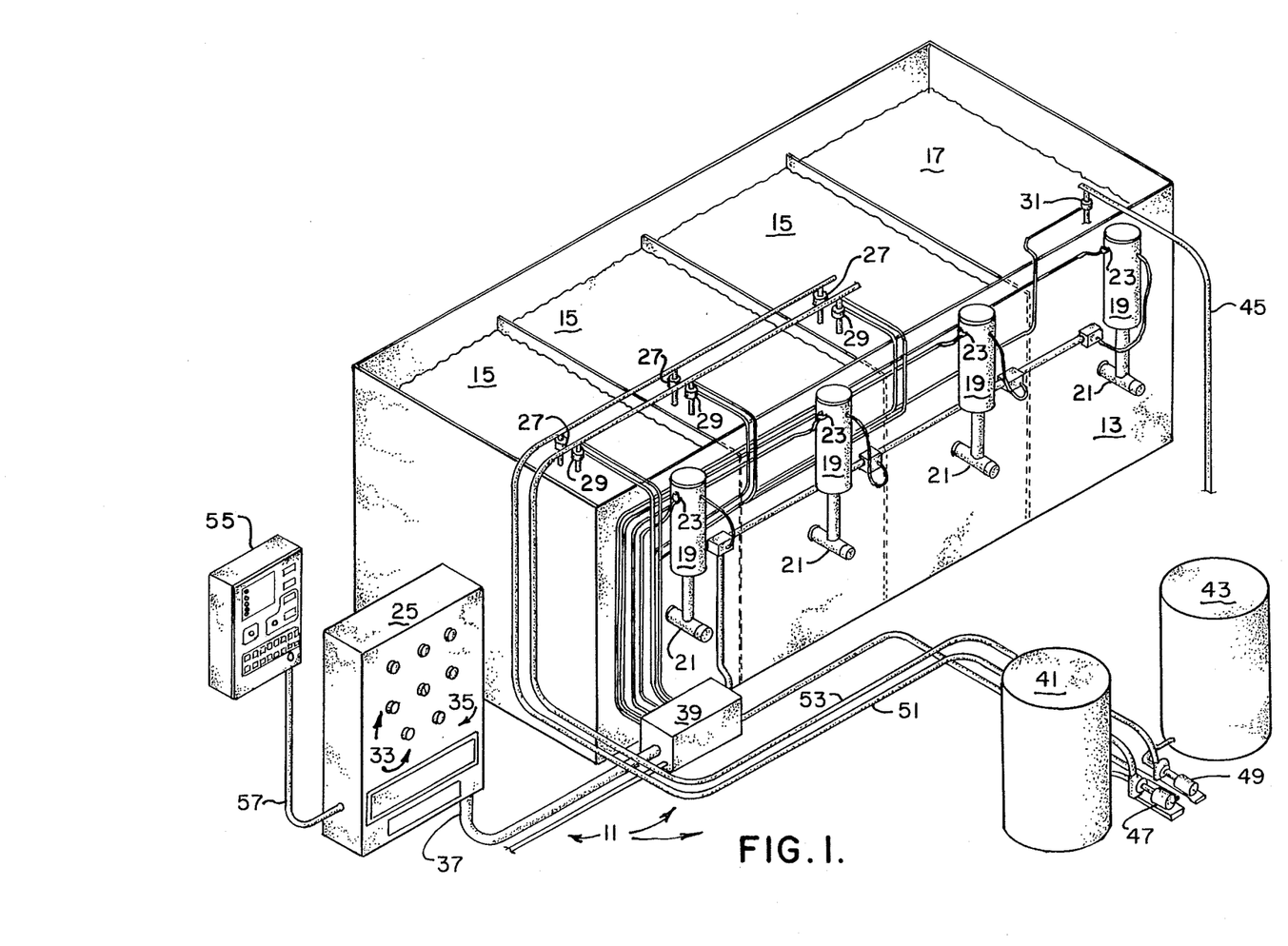
FIG. 1 is a perspective view of the caustic monitoring and control system of the present invention used in connection with a bottlewasher.

A caustic monitoring and control system 11 of the present invention is particularly adapted for use in connection with a bottlewasher 13 (FIG. 1). Bottlewasher 13 includes a series of tanks or compartments 15 containing a caustic soda solution usually in the range of 3.5% to 5.5% caustic followed by one or more tanks 17 of rinse water. In the embodiment of bottlewasher 13 shown, there are three caustic solution tanks 15 and a single rinse water tank 17 although the present invention is not so limited. Monitoring and control system 11 is designed to monitor and control the caustic strength as well as the liquid level in each tank. In order to perform these functions, each bottlewasher tank 15 or 17 as appropriate has attached thereto a sensor assembly 19 which is mounted externally beside the tank or compartment which is to be monitored.

Each sensor assembly 19 is mounted in a vertical orientation at such an elevation with respect to its tank that the normal operating liquid level in its tank falls approximately midway up the sensor assembly. The sensor assembly is connected to its tank by means of a single pipe connection 21. Each pipe connection 21 attaches to the side of its tank through a suitable fitting, and there may optionally be a manual isolation valve (not shown) provided if desired. In normal operation, such an optional manual isolation valve would be open, allowing free passage of the liquid in the tank to and from its sensor assembly 19. The level of the liquid in each sensor assembly 19 rises until it reaches equilibrium with the liquid level in its respective tank.

Each sensor assembly houses probes, described below, used by system 11 to monitor liquid level and solution strength. Each sensor assembly is mounted externally for several reasons. For one, this external mounting protects the probes from the sludge and debris which accumulate inside a bottlewasher. In addition, it isolates the liquid level sensing probes from the wave action normally present at the liquid surface inside its tank. In addition, external mounting avoids the physical constraints which would be imposed upon any internal location and it also provides easy access for maintenance.

In order to ensure that the sample tested by each sensor assembly 19 is actually representative of the solution inside its respective tank at the time the sample is tested, each sensor assembly 19 is periodically purged and a fresh sample of solution is allowed to enter that sensor assembly. This is accomplished by means of compressed air, or some other suitable fluid, which enters its respective sensor assembly through an air line fitting 23 suitably mounted to its respective sensor assembly. Each sensor assembly forms a sealed chamber having its only two outlets through fitting 23 and pipe 21. When air is forced through fitting 23 into its respective sensor assembly 19, it forces the previous sample out of the sensor assembly through pipe 21. The compressed air is then allowed to bleed back out of sensor assembly 19 through the air fitting, which allows a new sample from the tank or compartment to enter the sensor assembly. Once the new sample enters a particular sensor assembly, all readings are taken for liquid level, caustic strength, and temperature. The system then selects the next tank as described below and purges the next sensor assembly and the process is repeated.

Caustic control and monitoring system 11 also includes a main control panel 25. This control panel contains the control circuitry which runs the program that governs system operation. It also includes a set of selector relays (FIG. 2) which are used to select the sensor assembly 19 corresponding to a particular tank whose concentration and level is to be sensed. These relays also select, for each of the caustic tanks or compartments, a pair of valves 27 and 29 (rinse water tank 17 has a single valve 31) associated with that tank. These valves are air-operated. The main control panel also includes external control buttons, for example, reset and bypass buttons 33, displays or indicators 35, and the power supply for the system.

Because of the harsh environment around a typical bottlewasher (including high temperature, high humidity, and the possibility of chemical attack), main control panel 25 may be located as much as fifty to seventy-five feet away from the bottlewasher. It is connected to the rest of the system by a large diameter electrical conduit 37. More specifically, conduit 37 connects the main control panel with a solenoid valve housing 39 which houses solenoid valves used to operate the air-operated process valves 27, 29 and 31 and to control the compressed air used to purge sensor assemblies 19. The solenoid valve housing is typically located fairly close to the bottlewasher in a roughly central location. The wiring used to operate the solenoid valves contained in the housing runs from housing 39 to main control panel 25 through conduit 37. In addition, all necessary wiring from sensor assemblies 19 runs through this conduit to the main control panel.

System 11 also includes a pair of caustic supply tanks 41 and 43 from which caustic solution is drawn for the purpose of making adjustments to the solutions in the bottlewasher compartments 15. Tank 41 is a "low strength" supply tank which normally contains caustic solution equal to the strength nominally used in any given bottlewasher tank, typically 3.5% to 4%. Solution from this tank is used solely to make adjustments to the level of the solution in bottlewasher tanks 15. Tank 43 contains a "high strength" caustic solution, such as 25% caustic. Solution from this tank is used solely to adjust the strength or concentration of the solution in any bottlewasher compartment 15. It should be noted that changes to the level of rinse water compartment 17 are made not from tanks 41 and 43 but instead from a fresh water line 45 containing only fresh water instead of caustic.

When any additions of caustic are to be made from tanks 41 or 43 to compartments 15 of the bottlewasher, it is necessary to know precisely how much is being added. System 11 does this by timing the operation of a pair of dedicated positive displacement pumps 47 and 49. Pump 47 pumps low strength caustic from tank 41 to the desired ones of compartments 15, while pump 49 pumps high strength caustic from tank 43 to the desired one of compartments 15 of the bottlewasher. Of course, other types of pumps or feed systems along with a suitable flow meter could be used in place of positive displacement pumps 47 and 49 to add precisely controlled amounts of the desired caustic solution to any of compartments 15. Caustic flows from tanks 41 and 43 to the desired compartments 15 along piping 51 and 53 made of suitable materials and of an appropriate size to convey the caustic solution from the pumps to the various bottlewasher tanks. It should be appreciated that the particular material chosen for the supply piping would depend upon the particular caustic being used. In addition, the size of the piping is selected so that the amount of caustic from tank 41 or 43 may be accurately controlled. As described above, only one tank is selected at a time for the addition of caustic by the opening of its appropriate process valve 27 or 29. Suitable means (not shown) are employed for each compartment to provide a vacuum break and to prevent the caustic solution from coming into direct contact with the bottles being cleaned in order to prevent glass breaking from thermal shock.

As mentioned, air operated process valves 27, 29 and 31 are used to select one compartment at a time to receive an additional low or high strength caustic, or water, as appropriate. The use of air operated valves eliminates the potential hazard of using electric wiring (given the environment in which the system operates). There is also an additional benefit to using air operated process valves. These valves generate relatively high opening and closing forces compared to electrically actuated process valves, which greatly increase the system's reliability.

System 11 also optionally includes a monitoring panel 55 which allows the user to obtain a readout of the actual caustic strength and the temperature of any compartment on bottlewasher 13, as well as to monitor any alarm conditions. This may be done from a remote location such as the quality control lab. The monitoring panel 55 is connected by a conduit 57 to main control panel 25 and may be located a great distance therefrom. Monitoring panel 55 is described in detail in connection with FIG. 12 below.

Figure 2:
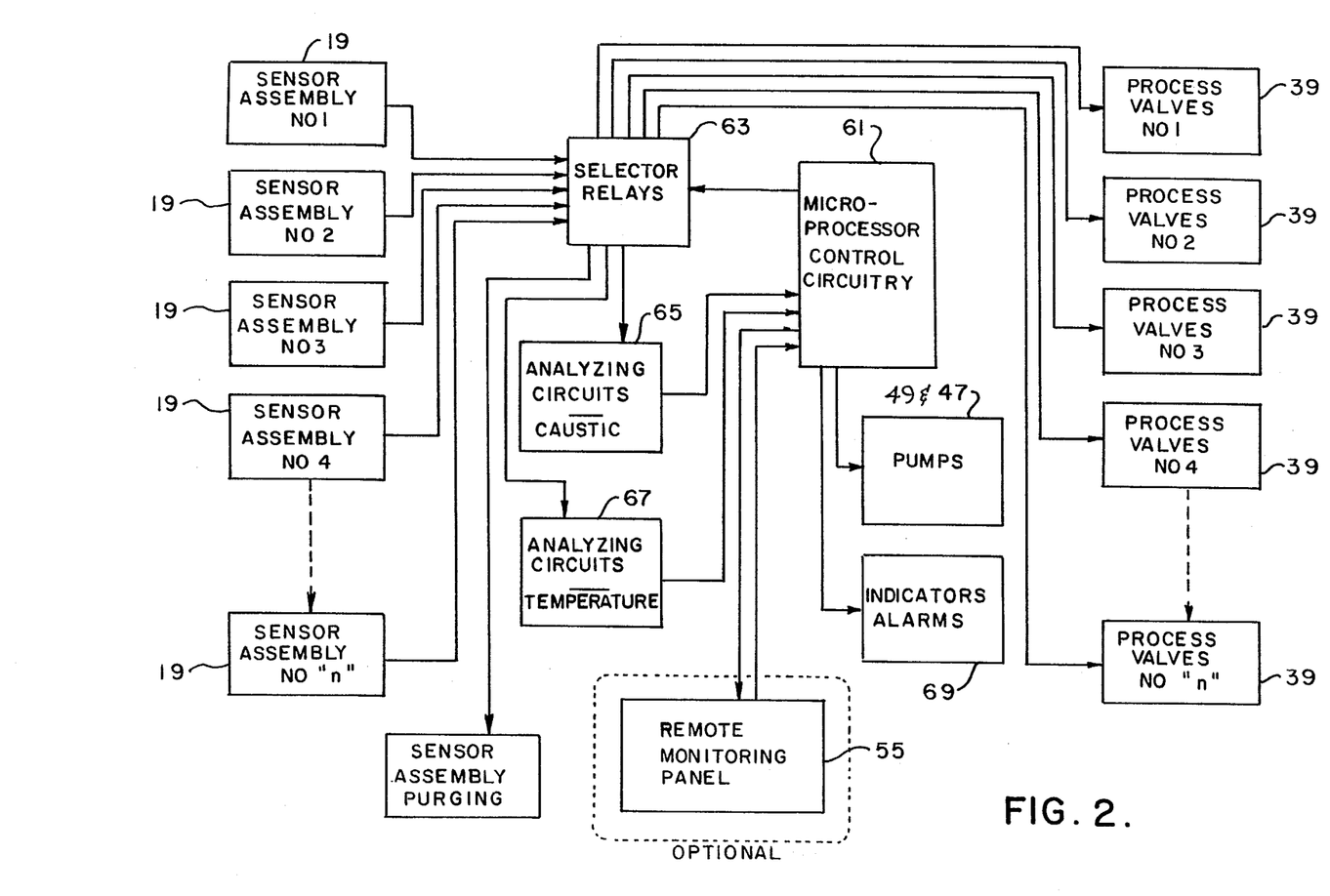
FIG. 2 is a block diagram of sensing and control portions of the system of FIG. 1.
Figure 3:
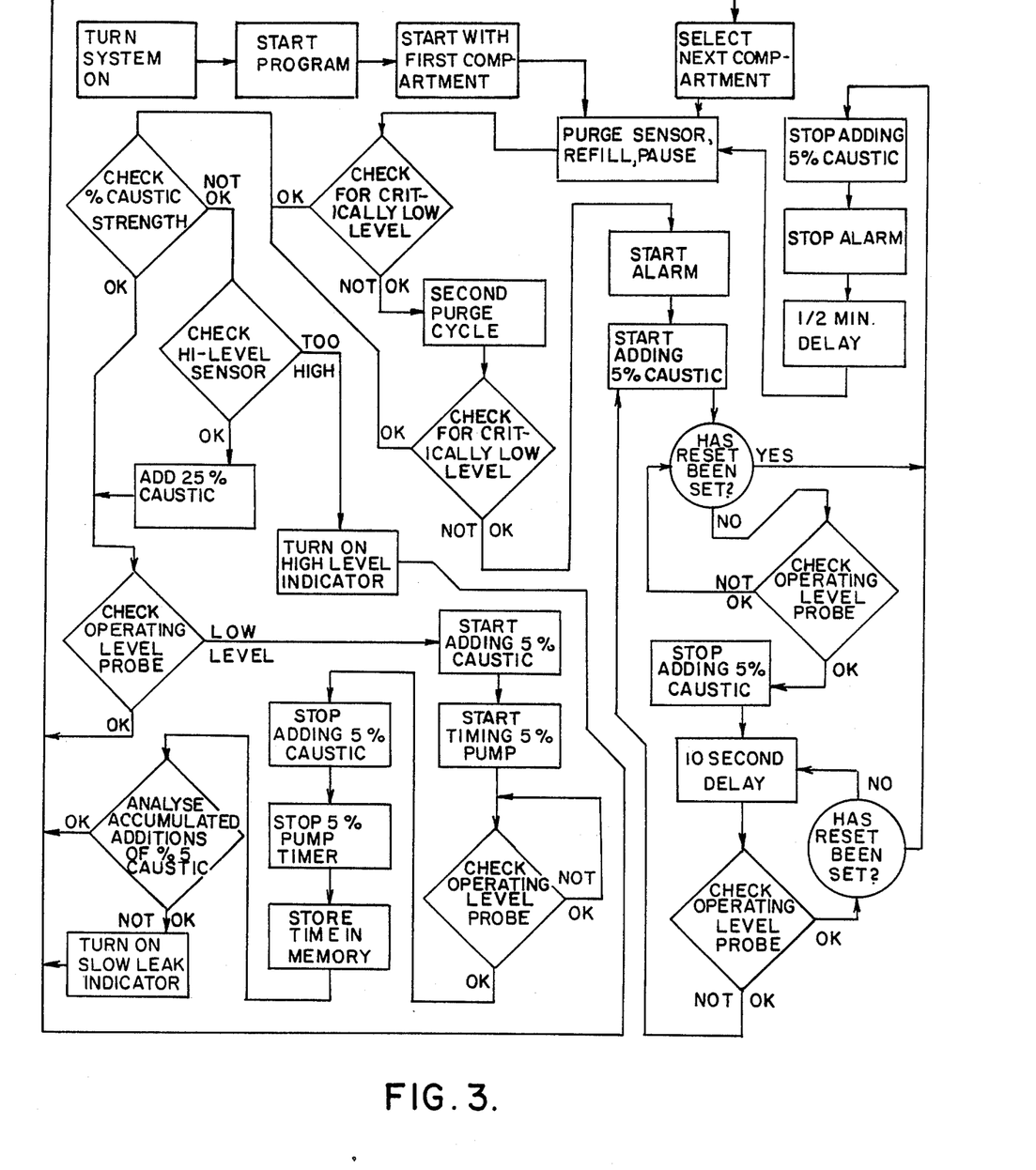
FIG. 3 is a flowchart illustrating the operation of the system of FIG. 1.

The operation of system 11 is controlled by microprocessor control circuitry 61 (FIG. 2) running the system in accordance with the flowchart of FIG. 3. This control circuitry could be a dedicated controller, but it is by no means essential that it be so. Other means such as relay logic or a programmed logic controller or even a full-fledged computer could be used so long as the flowchart of FIG. 3 is performed. The particular choice of microprocessor control circuitry 61 has no direct bearing on the present invention.

Microprocessor 61 selects a given tank or compartment 15 or 17 by means energizing the appropriate one of a set 63 of selector relays, which relays connect the sensors in sensor assemblies 19 corresponding to that compartment to analyzing circuits 65 and 67. At the same time, the particular selector relay 63 also connects the solenoid valves in housing 39 associated with that same compartment to the control circuitry to provide for the purging of the appropriate sensor assemby 19 and to prepare to make additions to the compartment as required. There is one eight-pole relay for each tank or compartment to be monitored and controlled. However, other configurations of relays can be used. Solid-state switching devices are preferably not used to select different sensor assemblies 19, however, because their relatively high internal resistance would alter the readings obtained from the probes in the sensor assemblies.

In addition to directly control the selector relays to select the proper compartment, the microprocessor control circuitry 61 directly controls pumps 47 and 49. The outputs of control circuitry 61 switch on the pumps as necessary by energizing a set of normally open contacts on the pump motor starter relay of the appropriate pump. The microprocessor control circuitry is also connected to a series of indicators and alarms 69 which are used to energize any desired combination of visual and audible alarms suitable to alert the operator of any of the various alarm conditions discussed below. Of course, as shown in FIG. 2, the system is not limited to the four compartments shown in FIG. 1. There can be any number "N" of sensor assemblies and process valves for "N" separate and distinct tanks. The number "N" can vary widely depending upon the particular bottlewasher being used but is generally between three and sixteen for the present embodiment of system 11.

System 11 can encounter various conditions during operation. For example, in each compartment the system is capable of detecting four different liquid level conditions. These conditions are illustrated graphically in FIG. 4. The first condition is the High Level condition, which refers to any level of the solution in the compartment being tested which is high enough to be detected oy a High Level probe 71 the tip of which is typically about ½ inch below the overflow of that particular compartment. When the level of the solution in the compartment is below the High Level probe but above the lower end of a second probe 73 called the operating level probe, it is in a zone referred to as the Operating Level. If the level is below the Operating Level but still above the levels of a pair of probes 75 and 77 which, as described below, are used to determine the conductivity or caustic strength of the solution, it is referred to as a Low Level condition. The Low Level condition occurs normally from time to time and is no cause for concern unless the occurances are too frequent. Typically this Low Level condition just requires "topping up" the tank to the Operating Level. The fourth condition is when the level in the tank is so low that probes 75 and 77, the caustic strength probes, cannot obtain a reading. This is referred to as a Critically Low Level condition. This condition is cause for alarm since it cannot be immediately determined how low the level actually is, and if the level is low enough, it can result in severe damage to the bottlewasher in a very short time. Still referring to FIG. 4, it should be noted that a fifth probe 79 is included in each sensor assembly. Probe 79 is a common probe and is used in connection with high level probe 71 and operating level probe 73. These five probes are suitably mounted in a head mounting block 81 disposed inside its respective sensor assembly 19 as described in more detail below.

There are also two caustic strength conditions which system 11 senses. The first is when the caustic strength of the solution is at or above the predetermined set point for that particular tank. For this condition system 11 does nothing. The second condition is when the solution strength is too low. In this condition high strength caustic from tank 43 must be added. Of course in the case of rinse water tank 17, these conditions are reversed since only a very low concentration of caustic contamination can be tolerated before more fresh water must be added for dilution.

System 11 handles these various conditions as described in the flowchart for microprocessor control circuitry 61 shown in FIG. 3. In examining the flowchart of FIG. 3, first assume that the readings from sensor assembly 19 for a particular compartment 15 or 17 are such that the liquid level is in the Operating Level range and the solution strength is acceptable. The system is turned on and the program has been started. The circuitry 61 selects the first tank or compartment. The previous sample is purged from the sensor assembly 19 by the introduction of compressed air or suitable fluid through air fitting 23 and the system than pauses for a sufficient length of time to allow a fresh sample of solution to enter that particular sensor assembly 19. Circuitry 61 then checks for the Critically Low Level condition. This involves probes 75 and 77 which are subsequently used to determine the solution strength. In this particular example, the probes 75 and 77 do obtain a reading, which means that the liquid level is not critically low. Next, it uses the same two probes to check the solution strength. Assuming that this strength is also satisfactory, the system then checks the operating level probe 73. Since the level in this example is within the operating level range, no further tests or actions are required. The circuitry 61 then selects the next compartment 15 and the process begins again.

For the second example, assume that the operating level is again satisfactory but that the solution strength is not acceptable. In this case, the addition of 25% caustic is needed to boost the solution strength. In the flowchart of FIG. 3, the step of adding caustic is actually a seven step process made necessary due to the particular needs of positive displacement pumps and air operated process valves in order to avoid pressure extremes in the system. These steps are as follows: Send a signal to open the appropriate process valve 27 or 29. Wait a few seconds to allow the appropriate valve to open fully. Send a signal to the appropriate pump 47 or 49 to turn the pump on. Allow the pump to run the predetermined amount of time. Turn the pump off. Wait a few seconds to allow the appropriate pump to fully stop. Close the appropriate process valve.

Before making the addition of 25% caustic in this example, the system checks the high level probe 71 to make sure that there is enough room in the tank for the added caustic without causing the tank to overflow. Since the level is within the operating level range, high level probe 71 obtains no reading so the addition of 25% caustic is made. The amount of 25% caustic which is added is a predetermined amount for each compartment so that the addition of high strength caustic is exactly enough to raise the solution strength in that particular tank by 0.1% (by way of example only). That amount is translated into the time the pump must run to pump that volume of high strength caustic. These times are stored in the microprocessor control circuitry memory. The system control circuitry then checks operating level probe 73. If this probe obtains a reading, no further action is required and the control circuitry selects the next tank and the program begins again.

Now assume that when high level probe 71 was checked, there was a High Level condition. In this case the high level indicator or alarm is turned on and the system takes no further action with respect to this compartment. The addition of the 25% caustic which was called for was not made. The system then selects the next compartment and the program begins again.

As another example, when control circuitry 61 checked the operating level probe 73, if the system could not obtain a reading, that would indicate a Low Level condition. Note that this is not a Critically Low Level condition, since at that point in the program the Critically Low Level condition had already been checked for and not found. In this case, control circuitry 61 restores the liquid level back to the operating level and, in addition, it looks at the total number of additions made to that tank 15 over a predetermined period of time to see whether the total additions fall within a normal range, or are great enough to indicate a possible slow leak. To perform the step of restoring the liquid level, circuitry 61 turns on low strength caustic pump 47 and while it is running, monitors the operating level probe 73 to determine when to stop the pump. At the same time, it times the pump to determine how long the pump had to run to restore the level or, in other words, to determine what amount of caustic solution was added to the tank. The pump running time is stored in a memory register in circuitry 61 which accumulates the running time for both pumps (pumps 47 and 49) for all additions made to that particular compartment during a predetermined period (such as twenty-four hours). That information is used to perform the second function, namely the detection of slow leaks.

In determining whether or not a particular compartment has a slow leak, one should keep in mind that some loss of solution is entirely normal and expected and should not be cause for concern. For each compartment one must independently of system 11 develop a figure representing the maximum losses which can be accepted during any given period such as 24 hours before one should consider the possibility of a slow leak. This figure would be developed by the operator of the bottlewasher through experiment and forms no significant part of the present application. Once such a figure is determined, it is translated into a theoretic maximum pump running time and is stored in the memory of microprocessor control circuitry 61. The microprocessor then compares the total pump running time for a given period to the theoretic maximum pump running time. If the actual time exceeds the theoretic maximum during any given period, a slow leak indicator or alarm is switched on for that particular compartment. It then stays on until either the next time period (for example, twenty-four hours) passes without the same condition arising again, or the alarm is reset. At the end of each such time period, the contents of the register or memory location in the which the actual pump running time is accumulated must be reset to zero and started over again. The actual time interval should be chosen to be at least approximately eight hours to assure that enough samples have been taken to permit reasonable accuracy, but it should not greatly exceed one day or the response to a real leak would be too long in coming. The slow leak detection feature requires two memory registers for each tank, which registers are dedicated to the task of storing the theoretic maximum pump running time and the actual pump running time. For example, assume for a particular compartment it has been determined experimentally that any losses in excess of seventy-five gallons in any twenty-four hour period should be considered a slow leak. If the positive displacement pumps 47 and 49 have a capacity of twenty-five gallons a minute, the pump running time to supply seventy-five gallons is 180 seconds. If within a given twenty-four hour period on this particular compartment, the system makes the following additions:

| | |
|---|---|
| 1. One addition of 25% caustic, 40 gallons | (96.0 seconds) |
| 2. One addition of 5% caustic, 15 gallons | (36.0 seconds) |
| 3. One addition of 5% caustic, 11 gallons | (26.4 seconds) |
| 4. One addition of 5% caustic, 14 gallons | (33.6 seconds) |
| TOTAL TIME: | 192.0 seconds | then with the third addition of 5% caustic, the total actual time would exceed the theoretic maximum of 180 seconds and system 11 would turn on the slow leak indicator or alarm. At the end of the twenty-four hour period, the accumulation register is reset to zero. The slow leak indicator, however, remains on until it is manually reset, or another twenty-four hour interval passes without a slow leak being evident. After checking for a slow leak, system 11 then continues by selecting the next compartment and beginning the program again.

The last part of the flowchart is that which is followed when the Critically Low Level condition is detected. This condition is detected when caustic strength probes 75 and 77 are unable to obtain any reading, which means that the liquid level in the tank is lower than the bottom of those two probes. This is potentially the most serious fault that system 11 can detect. A sudden, rapid loss of liquid or solution can indicate a major mechanical problem in itself, and can also in turn cause even more severe damage if left uncorrected for a period of as short as twenty minutes. Because of the serious nature of this condition, it has the highest priority alarms, both audible and visual. Accordingly, to avoid false alarms, the program's first response when the Critically Low Level condition is first detected is to purge the corresponding sensor assembly 19 and retest, in case the problem was a simple matter of some debris blocking the inlet to the sensor assembly. If the second test still fails to detect solution, the alarms are switched on and the low strength caustic pump 41 is turned on to attempt to restore the missing solution. As pump 41 runs, the system 11 monitors the operating level probe 73. If the level of the solution is restored to the proper level, pump 41 is shut off. But the alarms stay on and system 11 continues monitoring the operating level probe 73 in case the level drops again. If the alarm is manually reset, pumping and monitoring cease, and the alarm stops. In this case, however, the program does not carry on by selecting the next compartment. Instead, after a brief wait, it resumes by rechecking the same compartment to guard against the possibility that someone may press the reset and silence the alarm without correcting the problem that caused the condition.

There are also included in the system pressure switches (not shown) at the discharge of each pump 47 and 49. At any point in the program of FIG. 3 where the pumps are activated, the program will automatically interrupt pumping if the pressure switch for that pump detects a loss of pressure. The system thereupon turns on an indicator and halts. A program reset is then required to start the system operating again. This feature protects pumps 47 and 49 in the event caustic supply tanks 41 and 43 run empty while the system is running the pumps. It also provides protection in the event of several other mechanical problems which are possible although not highly likely.

The program for system 11 when it is dealing with rinse water tank 17 is similar to that of FIG. 3 but differs somewhat therefrom because the system must obviously respond differently in the rinse water tank than with the caustic solution tanks 15. This fact is incorporated into the program as follows: First, as each tank is selected, there is an identifying code which the program can check at the appropriate points of the program to determine if the tank currently selected contains water or caustic solution. The first point at which the distinction is necessary is where the system checks the caustic strength. The outputs from analyzing circuits 65 must be interpreted in exactly the opposite sense in the case of a rinse water compartment. Thereafter in the program, whenever an addition of caustic solution would usually be called for, the program again checks to see if the present compartment is a water tank. If it is, instead of opening a process valve and turning on a caustic pump, the system merely opens the appropriate process valve 31 on that tank which allows water from fresh water supply line 45 to enter the tank. Also, in the case of the water compartment, no matter whether the system calls for an addition for the purpose of diluting the concentration of the caustic in the rinse tank, or if it calls for an addition for the purpose of restoring the liquid level in the tank, the same fresh water supply line 45 and process valve 31 are used.

In the event that caustic monitoring panel 55 is used with system 11, the program of FIG. 3 must be further modified. In addition and additional analyzing circuit, described below, is required. In practice, the program first takes a reading from this extra analyzing circuit, stores the value in memory in order that it can be called up for display on the optional monitoring panel 55, and then takes the usual reading which is used by the system 11 to determine if an addition may be made to alter the strength of the solution.

In addition to the features described above, the user of system 11 has the option of having the system skip any desired compartment or compartments. On main control panel 25 is a series of bypass switches (for example, three of switches 33), one for each tank. After system 11 selects the new compartment or tank, purges it, and takes a temperature reading if desired, it then checks the bypass switch status for that particular compartment. If it is on, the microprocessor control circuitry 61 under program control then proceeds directly to the next compartment. By having system 11 purge the sensor assembly 19 before checking for the bypass status, the possibility of dirt and scale build-up on the sensor probes and in the sensor assemblies themselves, which could occur if the tank were on bypass for an extended period, is avoided.

Figures 4, 5:
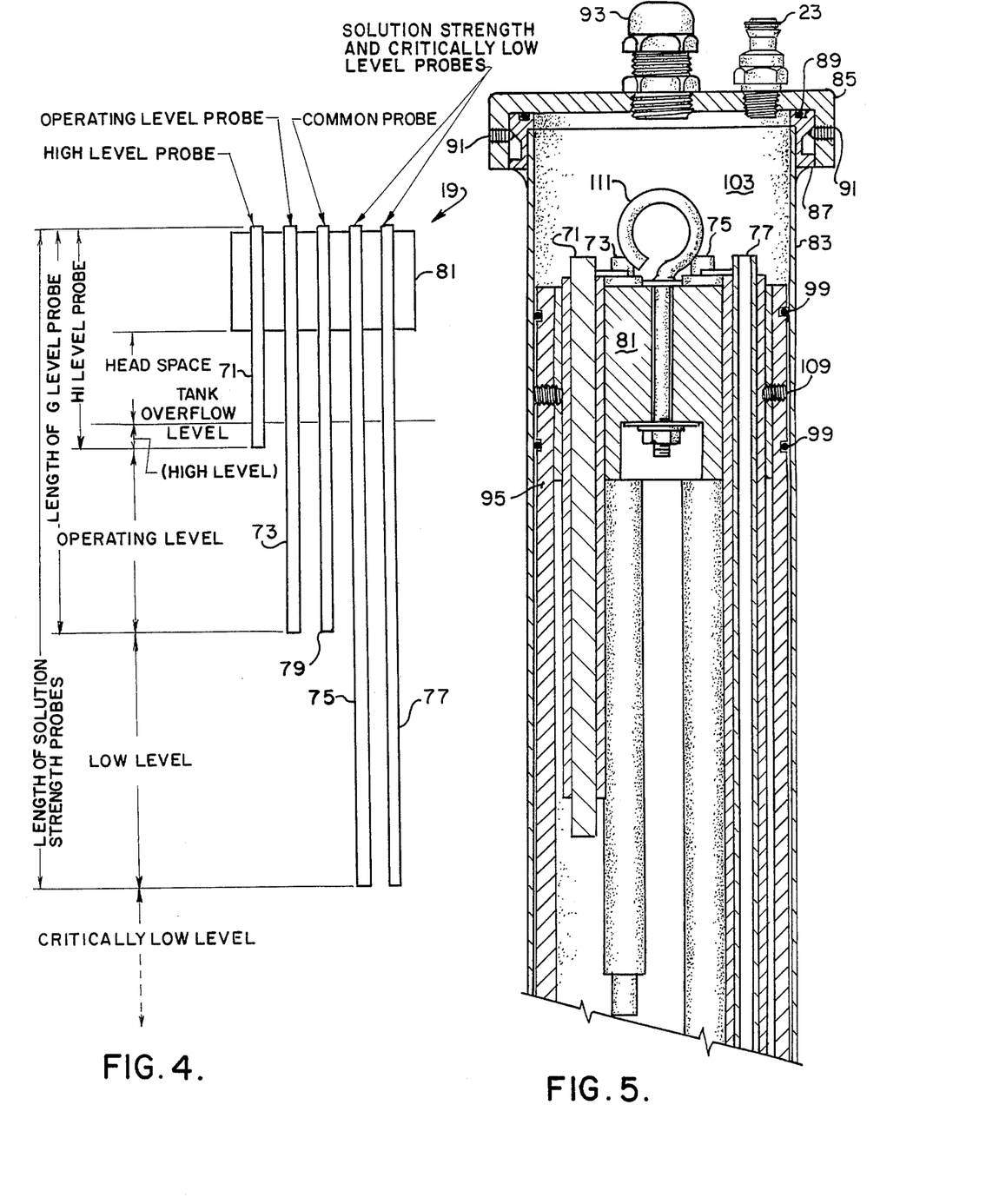
FIG. 4 is a schematic illustrating conditions sensed by the sensor probes of the present invention.
FIG. 5 is a sectional view illustrating the interior construction of the sensor assembly of the present invention.

Each sensor assembly 19 houses all of the probes 71, 73, 75, 77, and 79 used by the system to monitor liquid level and solution strength for its corresponding tank. Each sensor assembly includes an outer barrel 83, a cap 85, and a closure ring 87 suitably disposed between the outer barrel and the cap. A liquid-tight seal is formed between the closure ring and the cap by suitable means such as an O-ring 89. Air line fitting 23 may be disposed either in the outer barrel 83 as shown in FIG. 1 or in cap 85 as shown in FIG. 5. Cap 85 is secured to closure ring 87 by means of 6 set screws 91 or the like and the closure ring is suitably secured as by welding to outer barrel 83. Except for a cable fitting 93 in the cap of the sensor assembly as shown in FIG. 5 (or in the side of the sensor assembly as shown in FIG. 1), which is needed to pass electrical wires into the interior of the assembly, the only openings to the inside of the sensor assembly are the base fitting to which pipe 21 is connected and the air line fitting 23 in the top cap. Thus, when air is supplied to air line fitting 23 under pressure, it pressurizes the interior of that sensor assembly 19, forcing any solution in the sensor assembly back out into its corresponding compartment. Similarly, after the pressure is removed the remaining air in the assembly vents back out air line fitting 23.

Inside the hollow outer barrel 83, which is made of metal or some other suitable material, is an inner assembly which supports probes 71, 73, 75, 77, and 79. This inner assembly consists of a casing 95 and sensor mounting block 81 which is pressed into the upper end of casing 95. This mounting block is generally cylindrical and therefore disc shaped and has each probe fixedly secured thereto. It is cemented in place to prevent further movement of the sensor mounting block with respect to the casing. Both the casing and the sensor mounting block are made of CPVC plastic, which is an excellent electrical insulator and is unaffected by caustic solutions in the concentrations heretofore mentioned. Between the outer cylindrical surface of casing 95 and the inner surface of outer barrel 83 there are four O-rings 99 (only the top two of which are shown) positioned in grooves machined into the outer surface of the casing. These O-rings serve to support the casing inside outer barrel 83 and provide a seal between the two to divide the inside of the sensor assembly into two portions, a sensing chamber below and inside the casing, and the remainder of the interior of the sensor assembly above the casing assembly.

The assembly made up of casing 95, sensor mounting block 81, and its associated probes may be raised or lowered with respect to outer barrel 83 to "fine-tune" the height of the probes with respect to the liquid level in the tank. Once the desired position has been established, an appropriately sized spacer (not shown) is installed in the bottom of barrel 83 below casing 95 to allow it to maintain the correct height inside the sensor assembly. In practice, the liquid sample height would never reach as high as the bottom of sensor mounting block 81.

The compressed air which displaces the previous sample in the sensor chamber defined by casing 95 and sensor block 81 passes from the upper chamber, labeled 103, through probes 75 and 77 and through a small, small vent passage (not shown) drilled through the sensor mounting block 81. This vent passage is needed to prevent a pocket of trapped air forming up inside casing 95 above the level of the ends of open-ended probes 75 and 77. As can be seen from FIG. 6, probe 75, and also probe 77, are hollow their entire length, which permits air to flow freely therethrough and also permits solution being tested to flow up into the probes themselves.

The probes in each sensor are of two types. The probes of the first type, represented by probes 75 and 77, are used to measure solution strength or concentration and are distinguished by their hollow, inner stainless steel tube electrodes. Probes of a second type, represented by probes 71, 73, and 79, are used in the determination of liquid level and employ a solid stainless steel inner electrode. Both type of probes have a wire terminal welded to the side of their stainless steel electrodes at their upper end and both are sheathed in a CPVC plastic outer sleeve. On the hollow type probes, the outer plastic sheath extends down a predetermined distance such as four inches beyond the end of the metal inner electrode. For example, in FIG. 6, the outer sheath is labeled 105, while the stainless steel inner electrode is labeled 107. On the solid type probe, the outer plastic sheath is shorter than the inner metal electrode so that the electrode is exposed for its last one-half inch of length or so. Note that the hollow probes can also be used for determining liquid levels, but the solid probes cannot be used for determining solution strength in this particular invention.

The probes are made in various lengths to work with various sized compartments. The compartment capacities and physical dimensions must be known before the probe lengths can be calculated. Therefore, each set of probes may be custom made for a specific compartment. However, the relationship of the length of one probe to another within a set is generally fixed.

Probes 71, 73, 79, 75, and 77 are mounted in sensor mounting block 81 in a generally circular array as seen as from the top of the mounting block. They are secured in position by means of set screws 109 (FIG. 5). Each probe is positioned so that its plastic sheath protudes above the level of the top surface of the sensor mounting block by about one-eighth inch so that should a small amount of moisture or condensation collect in upper chamber 103, it will not cause an electrical short-circuit between the probes. An eyebolt 111 is provided to allow the entire inner assembly to be removed from outer barrel 83 if the need should arise. Not shown in FIG. 5 are the five wires extending through cable fitting 93 to each of the various probes. Cable fitting 93 provides a watertight closure around the cable which carries these probe wires.

An example of the lengths of the various probes follows: Typically, the length of the shortest probe, high-level probe 71 is $\frac{3}{8}$" plus the length of the sensor block 81, plus 2" head space plus $\frac{1}{2}$", which for a typical application could be approximately 5.4". Of course, the actual length of any of the probes can be varied at will without disturbing the overall concept of the present invention. To determine the spacing required between high-level probe 71 and operating level probe 73, one must consider two phenomena. First, some allowance must be made for at least a small amount of wave-action or slosh being present inside sensor assembly 19, because in most cases there is not any adequate method to totally shield the sensor assembly from the agitation in the bottlewasher compartment 15 or 17. For the sake of this example, let that allowance by $\frac{1}{4}$". The second factor to consider is the change in level which will occur in the tank, and of course in the sensor assembly, whenever there is a gap or space in bottle flow. At any given time, depending upon the size of the bottlewasher, there are hundreds of bottles submerged in the solution in any one tank. The volume of glass which comprises these bottles displaces an equal volume of solution. If the flow of bottles into the washer is interupted, which is a common and natural occurance, the liquid level in the affected compartment drops. It would be less than ideal if system 11 were to respond to such a normal event by adding solution only to have it overflow the compartment when the flow of bottles resumed. Accordingly, the change in level caused by the "bottle vs. no bottle" effect must be determined for each compartment to be monitored and allowed for in the probe spacing. This level change is referred to as the bottle allowance. Aside from these two effects just described, the primary factor involved in determining the operating level spacing is the space involved for the purpose of making additions to the tank to change the solution strength. System 11 is designed to make additions which will alter the concentration by 0.1%. For each tank, it must be determined what change in level will occur when such an addition is made. If the design specification is that the system must be capable of correcting an error in concentration of as much as 0.5% without causing the tank to overflow, then the difference in length between the high-level and operating level probes must be at least five times the additional level change plus the bottle allowance plus the slosh factor. If for example, on one particular compartment, the change in level for one addition of 25% caustic results in a level change in the compartment of 0.625" and the bottle allowance is 1.25", the total difference in probe length must be at least 4.875". Continuing with the same example, if the high-level probe is to be at least 5.375" long, the overall length of the operating level probe 73 must be 10.25". The length of the common probe 79 can be the same as the operating level 73 or even longer. It is used with both the high-level probe 71 and the operating level probe 73 to complete the circuit in connection with the analyzing circuit of FIG. 9.

The most important factor in the length of the solution strength probes 75 and 77 is the requirement that there te at least one inch immersion of the metal inner electrode to insure accurate readings. Therefore, the difference in length between the solution strength probes and the operating level probe must be, at the very least, the slosh factor plus the bottle allowance plus one inch. However, in practice, it would generally be more common to also add a small additional allowance for the amount of loss which might be expected to take place normally from one reading to the next. That would ensure sufficient probe immersion of the solution strength probe 75 and 77 to ensure an accurate reading under even slightly low-level conditions. To continue the example from above, if this "low-level allowance" was one inch, the minimal overall length of the solution strength probe 75 and 77 would be 10.25" plus 0.5" plus 1.25" plus 1", which equals 13 inches. Note that all the lengths referred to so far are the lengths of the inner metal electrodes and not the length of the outer plastic sheath. Of course, these lengths are for purposes of example only and do not in any way limit the scope of the present invention.

Figure 6:
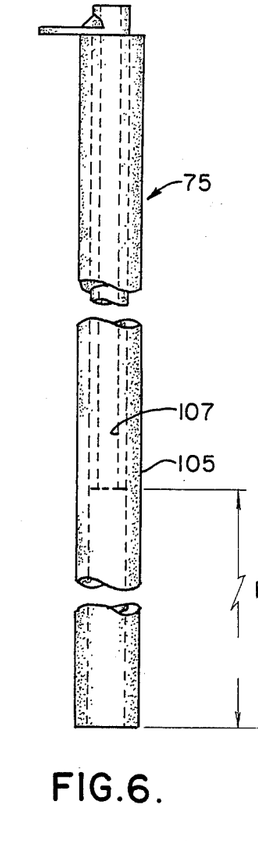
FIG. 6 is a front elevation of the conductivity probes used with the sensor assembly of FIG. 5.

The conductive element or electrode of probes 75 and 77 is a metal tube (FIG. 6). For example, electrode 107 is No. 304 stainless steel of 0.3125" diameter with a wall thickness of 0.065" and has an outer non-conductive sheath 105 made of CPVC plastic which extends beyond the metal probe for four inches. However, the precise composition and size of these elements are not critical to the present invention. Although as heretofore described, these particular probes have special application in determining the concentration of a caustic soda solution between 0.1% and 6.0% at temperatures up to 185° F., the principle of these probes may be applied advantageously wherever conductivity measurements of solutions are made. The hollow probe design allows conductivity measurements to be made where at present conductivity is believed to be difficult or impossible to measure.

Figures 7, 7A, 8, 8A:
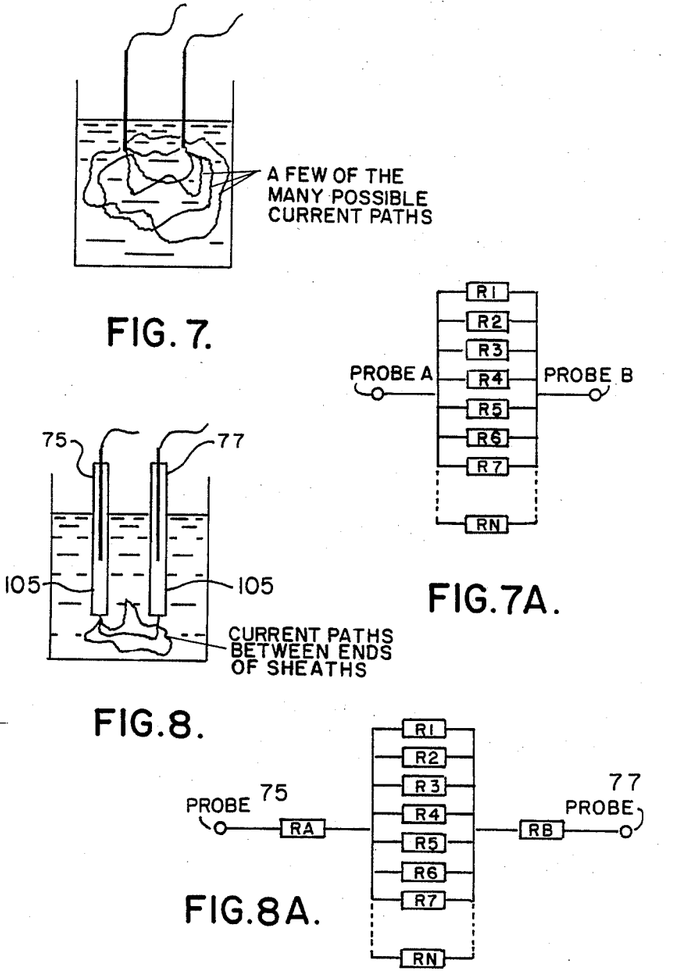
FIG. 7 is a schematic illustrating the operation of prior art conductivity probes.
FIG. 7A is an electrical schematic illustrating the resistance between the conductivity probes of FIG. 7.
FIG. 8 is a schematic illustrating the operation of the conductivity probes of the present invention.
FIG. 8A is an electrical schematic illustrating the resistance between the conductivity probes of FIG. 8.

Since inner electrode 107 stops a predetermined distance, for example, four inches short of the open end of non-conductive sheath 105, the probe has what will be referred to as a "controlled volume" which allows the probe itself to generate a stronger signal than would otherwise occur. This stronger signal allows it measure the concentrations of very weak solutions which could not be easily measured with conventional probes. It also allows one to easily and accurately discriminate between two solutions which vary only slightly in strength, on the order of 0.1% difference or even less. The reason for this increase in signal strength and accuracy is shown in FIGS. 7, 7A, 8, and 8A. As can be seen in FIG. 7, with a conventional pair of conductivity probes, the solution in which the probes are immersed act like a resistor. However, there are an enormous number of "paths" for current flow between the two probes. This situation can be simulated by the circuit of FIG. 7A which has an enormous number of resistors R1 through RN in parallel between a probe A and a probe B. Because these resistors are in parallel, the combined resistance of all these resistors is very small, even when the resistors are large individually. In FIG. 8, the controlled volume probes of the present invention are illustrated. The extended sheath 105 traps a controlled volume of the solution whose conductivity is being measured. Even though the sheath is open at the bottom, the current flow must pass through the solution within the sheath before it exits the bottom of the probe. Within the sheath, there are a strictly limited number of current paths related directly to the cross-sectional area of this controlled volume. Hence, the solution contained within the sheath can be characterized by a single resistor. For a given solution, the value of this resistor will increase as the length of sheath increases beyond the end of the electrode. For the present application, an extension of four inches is highly satisfactory. However, a broad range of lengths could be used satisfactorily, particularly for other applications.

Probes similar to that shown in FIG. 6 were tested using various lengths of sheath extension. These probes were used to test two actual solutions which had a solution strength difference of 0.17%. For comparison, using just bare metal electrodes, the difference in resistance between the two solutions was unmeasurable. When the electrode was flush with the end of the sheath higher resistances resulted, but the difference was still too small to measure practically. However, as the sheath was extended beyond the electrode tips, not only did the actual resistance measured increase, but the difference measured between the two solutions quickly grew. The results obtained for various lengths of sheath extension are shown in the following table:

| ACTUAL CAUSTIC SOLUTION STRENGTH | | |
|---|---|---|
| SHEATH POSITION | 2.78% SOLUTION RESISTANCE, OHMS | 2.95% SOLUTION RESISTANCE, OHMS |
| 1" extension | 137.1 | 128.7 |
| 2" extension | 200.3 | 189.8 |
| 3" extension | 271.2 | 257.4 |
| 4" extension | 338.7 | 324.7 |

Note that at the four inch extension, the difference in the resistance between these two solutions was fourteen ohms, a value of sufficient magnitude to make it practical to measure. Thus these results clearly indicate that increased signal occurs at the source as sheath 105 is lengthened past electrode 107. Simulating this arrangement with resistors gives the arrangement shown in FIG. 8A consisting of two large resistors RA and RB in series with a large number of resistors R1 through RN in parallel. The two resistors in series represent the effect of the controlled volume in the sheaths of probes 75 and 77, while those in parallel represent the remainder of the solution between the two probes. The resulting circuit may be reduced to a single resistor of equivalent resistance having a resistance of twice the resistance of the controlled volume plus the resistance of the free solution. Of course, in order to employ the principle of controlled volume, it is only necessary for one of the two probes to have the extended sheath in order for the effect to be apparent.

There is also some lesser resistance at the surface of each electrode 107. However, the effect of this resistance is minimized in the present design by making the probe and electrode hollow and stipulating that at least one inch of the electrode must be immersed in the solution so as to have a large surface area of the metal electrode in contact with the solution. There are also two other reasons why the electrode itself is hollow. One of these reasons is so that there will not be an air pocket trapped in the controlled volume when a fresh sample of solution is drawn into sensor assembly 11. The old sample is purged out by blowing compressed air through the probe. The probe is then allowed to vent through the hollow tube electrode so a new sample can enter without an air pocket. The other reason is that the compressed air used for purging the stale sample also has the effect of cleaning dirt, debris, or scum off metal electrode 107 and blowing it out of sheath 105.

An additional feature of system 11 which also minimizes the probe surface resistance is the fact that each probe 75 and 77, as well as the other probes, operate on AC current. This eliminates gasing or plating occuring at the probe's surface, which would otherwise alter the readings obtained by the probe. Of course, for other applications, it might not be necessary to use a hollow probe. Also, when the hollow probe construction is used, the cleaning action, described above, can easily be accomplished using other gases or fluids besides compressed air. For example, certain applications might involve a cleaning medium such as water, salt, or even more of the same fluid whose conductivity is being measured injected through the hollow electrode.

There are two different analyzing circuits (shown in FIGS. 9 and 11) which can be used with the probes heretofore described. Both circuits include a modified Wheatstone bridge and use alternating current inputs. Although both circuits may be operated on sine-wave alternating current, better results have been obtained with square-wave inputs.

Figure 9:
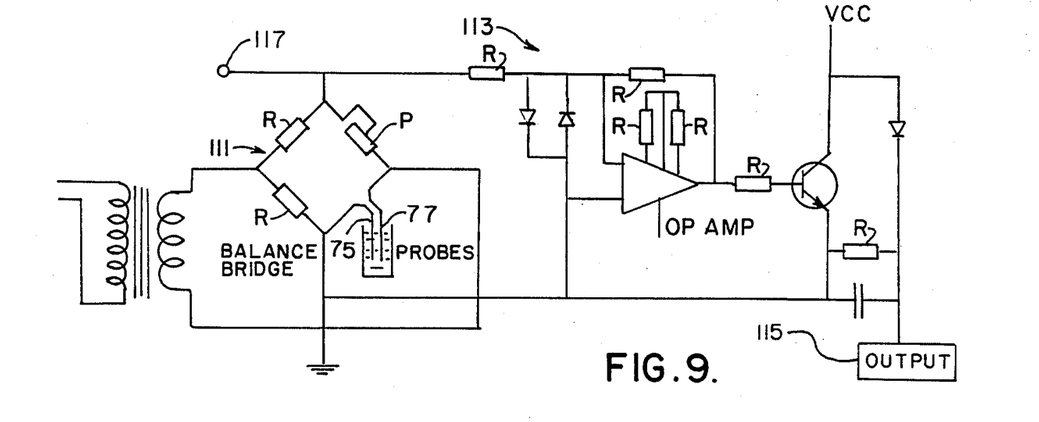
FIG. 9 is an electrical schematic illustrating a fixed point conductivity testing circuit of the present invention.
Figure 10:
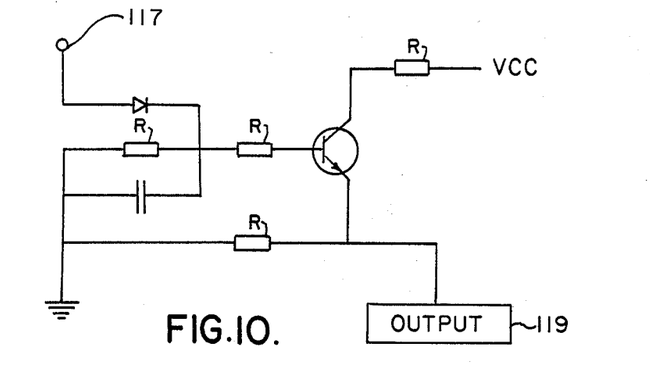
FIG. 10 is an electrical schematic illustrating a critically low level circuit detector of the present invention.

The analyzing circuit shown in FIG. 9 is a balanced bridge circuit. In this design the output of the circuit is switched either on or off, depending upon whether the resistance across the probes (namely, the resistance of the solution) increases above a set point or decreases below it. The practical application of this circuit is in a case such as the controlling of solution strength in a bottlewasher compartment. The Wheatstone brige, labeled 111, includes a pair of fixed resistors R, a potentiometer P, and a final leg of the bridge which includes two probes, such as probes 75 and 77, connected through the solution whose concentration or conductivity is being measured. Potentiometer P is manually adjusted so that when the resistance across the probes is equal to that which would be read when the solution is at exactly the correct strength and temperature, the bridge will balance, which means that the bridge output is zero. The bridge output is supplied to a switching circuit 113 of fairly conventional design which turns the output labeled 115 on or off. When the bridge output is zero, the switching circuit output is zero and the final output of the circuit is off. If the resistance at the probes vary from the set point, the bridge output will also vary, becoming either positive or negative, depending upon which way the resistance is varied. The switching section will pass only one polarity and not the other, switching on the final output 115 for the polarity that will pass. Obviously, this circuit can be rearranged slightly to respond only to increasing solution strength, or only to decreasing solution strength in relation to the set point, whichever is desired. Note that without further manipulation of potentiometer P, further testing, or a table of previously collected data, the balanced bridge analyzer circuit cannot be easily used to measure the actual strength of an unknown solution. It is, however, ideally suited for detecting the Critically Low Level condition described earlier. For this purpose probes 75 and 77 are connected in the analyzer circuit of FIG. 9 as shown. The output of the bridge is supplied via a terminal 117 to the circuit of FIG. 10 whose output 119 represents the Critically Low Level condition. If the liquid level is so low that probe 75 and 77 are not in contact with the solution, they will read an infinitely high resistance. This not only unbalances the bridge, but it does so at its peak output voltage. This voltage is supplied via terminal 117 to the circuitry of FIG. 10. The components of FIG. 10 are selected such that only such a peak voltage from bridge 111 can trigger an output at 119. That output is interpreted by the microprocessor 61 as an indication of critically low solution level.

The second analyzer circuit (FIG. 11) is called a linear bridge circuit. Unlike the balanced bridge circuit described above, this circuit may be used to measure the actual strength of an unknown solution, without further adjustments. Again, it includes a modified Wheatstone bridge 121 having a pair of resistors R and a potentiometer P. The final leg of the bridge again includes a pair of probes such as probes 75 and 77 in electrical contact through the solution being monitored. Instead of adjusting bridge 121 to a particular set point, it is adjusted so that the bridge will remain unbalanced throughout the entire range of solutions were are to be measured. A square-wave generator 123 supplies a square-wave to Wheatstone bridge 121. The output voltage of the bridge thereupon varies with varying solution strengths. The output of the bridge is then supplied through a precision rectifier 125 to an analog to digital converter 127 to provide a digital output directly representative of the output voltage of the bridge. Thus, through simple electronic manipulation, this output voltage can be converted by the microcomputer 61 to a direct numerical display of actual solution strength on the optional monitor 55. This reading can also be used by a microprocessor or computer 61 to determine when the system must make responses, such as altering or controlling solution strength, turning on an alarm or the like.

Figure 12:
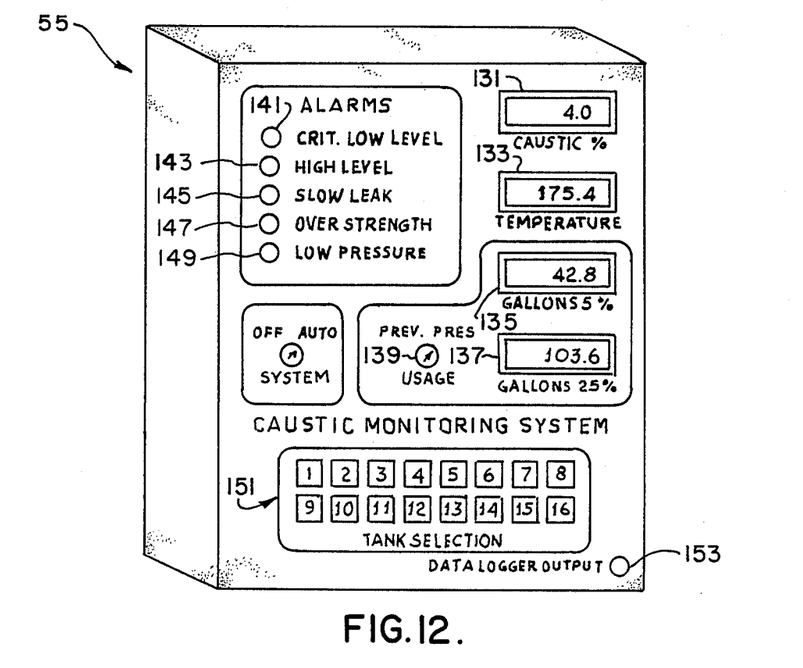
FIG. 12 is a perspective of a monitoring panel optionally used with the present system.

Turning to FIG. 12, caustic monitoring panel or remote monitoring panel 55 may be disposed either adjacent main control panel 25, or disposed in a remote location such as the quality control lab. Its use with system 11 is not mandatory. This panel allows the user to monitor system 11 at a distance, as well as provides additional readouts. Of course, the particular configuration of panel 55 shown in FIG. 12 could be varied, as could some of the information displayed, without altering the basic intent and function of the invention. The temperature display in particular is an independent function which could be accomplished through a variety of "off the shelf" hardware. The monitor panel 55 includes a display 131 for displaying the solution strength or caustic percentage, which display is selectable by compartment. A display 133 is provided for displaying the temperature by compartment. A display 135 displays the amount of low strength caustic used during the present measuring period, such as twenty-four hours, in gallons. A display 137 is also provided for displaying the gallons of high strength caustic used during the present measuring period. A switch 139 is also included in panel 55 to switch the displays 135 and 137 from displaying present usage to displaying the usage in the previous interval of twenty-four hours, for example. Panel 55 also includes a critically low level alarm 141, a high level alarm 143, a slow leak alarm 145, an overstrength caustic alarm 147 and a low pump pressure alarm 149. The critically low level alarm, the high level alarm, the slow leak alarm, and the overstrength caustic alarm conditions are also indicated not only with indicator lights 141, 143, 145, and 147, but also by a row or two of internally illuminated push buttons 151 bearing the compartment numbers thereon which indicate the alarms by tank number. The appropriate compartment push buttons are lit in conjunction with the alarm indicator light to identify on which compartment the problem is occuring. In the case of more than one type of alarm occuring at the same time on different compartments, each alarm indicator can be made to flash on and off at a distinctly different frequency and the corresponding compartment number light will flash in time with the alarm indicator.

Figure 11:
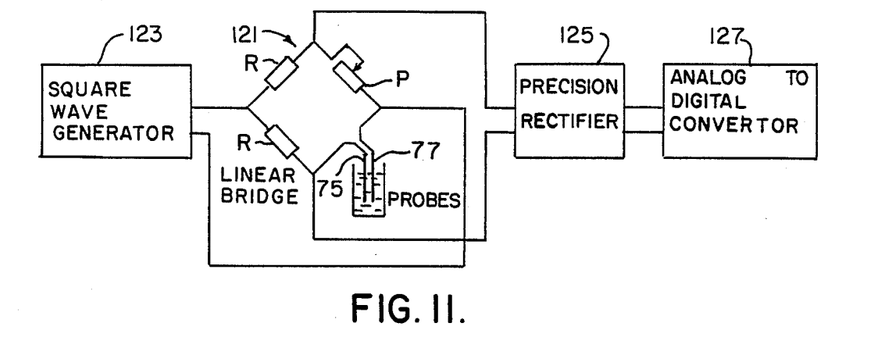
FIG. 11 is an electrical schematic in block diagram form illustrating an alternative to the circuit of FIG. 9.

The solution strength or caustic strength display 131 derives its information from system 11 using the linear bridge of FIG. 11 described above. As system 11 samples each compartment, the strength reading is taken and stored in memory. By storing all pump-running times in memory, the system 11 can also provide all four caustic usage figures. These figures are already stored for use in slow leak detection as described above. In order to have the usage for the previous measuring interval available, the final total usage at the end of each period must be stored in a separate set of memory registers before the registers for the present period are cleared to start the next interval.

Pressing one of the numbered tank select buttons 151 on panel 55 causes the most recent caustic strength and temperature readings be displayed for the corresponding tank compartment in displays 131 and 133, as well as the low and high strength caustic usage up to that point during the current measuring interval. Or, if the user so selects, the usage for that compartment from the most recent previous interval may be displayed instead. There is also an output terminal 153 on the face of panel 55 which allows a data recorder (not shown) to either record the results from each sampling, or the daily totals, or a combination of the two as required.

Caustic monitoring panel 55 communicates with main control panel 25 via a standard serial interface. The addition of caustic monitoring panel 55 requires the use of the linear bridge circuit of FIG. 11, as well as some additional software for its operation. Note that pressing one of the buttons 151 on the monitoring panel 55 does not in any way alter the sampling sequence or provide any control over system 11, but merely calls up the results of the most recent sample taken on each tank.

Although the present invention has been described as an entire system, it should be realized that the invention includes various subcombinations of system 11. For example, a simplified handheld meter with a set of probes 75 and 77 on the end of a short cable could be dipped into a solution of unknown strength and temperature and, after a few seconds, could display the concentration of that solution This handheld meter can use the linear bridge of FIG. 11 and a specially mounted pair of controlled volume probes 75 and 77. Such a meter would have no level checks, alarm indicators, automatically controlled purging, or any of the other features of the full-function system 11 previously described.

Alternatively, such a portable meter could be used in conjunction with a single output to control solution strength only. It would be mounted on a tank such as low strength caustic supply tank 41 which generally is filled with reclaimed caustic which often has to be brought back up to strength. Such a portable device would control the solution strength on just that one tank. Another application of such a device would be for controlling a swimming pool chlorinator.

As a third alternative, the system of the present invention could include the monitoring functions heretofore described but no control outputs. It would use the linear bridge of FIG. 11 and no balanced bridge circuits. It would also incorporate the caustic monitoring panel 55 of FIG. 12. Such a simplified system would use input data from flow meters on the caustic supply lines in order to supply any information on caustic usage since the system itself would not be controlling the supply line pumps. Such an embodiment of the present invention would be an effective alternative to manual sampling and titration in a situation where other considerations must be taken into account by the operator before making any additions to the tanks.

The fourth embodiment of the present invention is the system 11 as heretofore described without the optional caustic monitoring panel 55. Such a system is designed to handle from three to sixteen compartments, controlling the solution strength and liquid level, and providing alarms for various problems. It would make use of the balanced bridge circuit of FIG. 9, but not the linear bridge circuit of FIG. 11. By means of the individual potentiometers P for each set of probes, the user could set a different solution strength for each tank as desired.

In view of the above, it will be seen that the objects of this invention are achieved and other advantageous results obtained. As various changes could be made in the above constructions without departing from the scope of the invention, it is intended that all matter contained in the above description are shown in the accompanying drawings shall be interpreted as illustrative and not in a limiting sense.

What is claimed is:

1. A sensor assembly for use in conjunction with a sampling device operatively associated with a liquid storage tank in which a bottle washing or similar type function is performed and for use for testing the concentration of liquid samples contained therein, each sensor assembly including an outer casing, a cap means for said casing, and provide for substantially sealing its upper end thereof, electrical cable fitting provided upon one of said cap and casing for providing for extension of electrical wires therethrough, air fitting means provided upon one of said cap and casing for providing for conduct of air under pressure therethrough and for purging and previous liquid sample remaining within said casing, a sensor mounting block provided within the casing and displaced below the said cap, a plurality of sensor probes mounting through the said block and at their upper ends extending at least to the space between the said block and the said cap, while said sensor probes at their bottom ends extending downwandly at predetermined distances into the said casing, said casing at its proximate bottom end having an inlet for entrance of liquid samples therein, said electrical wires connecting with the upper ends of select of said sensor probes, a first of said sensor probes being a high liquid level probe for detecting the highest operating liquid level in the said liquid storage tank, a second of said sensor probes being an operating level probe for detecting a preferred operating liquid level in said liquid storage tank, said second sensor probe extending a predetermined distance further downwardly within said casing than said first sensor probe, the third and fourth sensor probes provided within said casing and functioning and cooperating with circuitry to detect and determine particular concentrations of the sampled solution therein, and one of said third and fourth sensor probes providing a determination of a critical low level of liquid within the said storage tank, and said third and fourth sensor probes extending further downwardly within said casing than said first and second probes.

2. The invention of claim 1 and including a fifth sensor probe extending downwandly within said casing equivalent to the depth of said second probe and functioning in cooperation with said third and fourth sensor probes to complete electrical circuitry to determine particular concentrations of the sampled solution contained within the casing.

3. The invention of claim 2 and wherein said sensor probes adapted to be at least partially emerged in the solution for providing for a measurement of its conductivity therein, said probes being arranged in a predetermined geometrical relationship with respect to each other, each of said probes having an outer, insulative sheath and an inner, conductive electrode, said electrodes being exposed to the solution at at least one point when their probes are immersed therein, at least one of the third and fourth electrodes being recessed a predetermined distance from an open end of its respective sheath so that the solution must fill a predetermined volume in the sheath corresponding to said predetermined distance before contacting the electrode, and said specificed probe including said one of said electrodes having a fluid path therethrough to permit solution to rise therein to the level of the said electrode, with the resistance between the said third and fourth sensor probes being a function of the conductivity of the solution between the two probes, the solution in the predetermined volume in the one probe providing a substantial portion of the total resistance between the two electrodes.

4. The invention of claim 2 and wherein said third and fourth sensor probes each formed having an outer insulative sheath and an inner, conductive electrode, with the electrodes of both the said third and fourth sensor probes being recessed a predetermined distance upwardly from an open end of their respective sheaths.

5. The invention of claim 4 and wherein one of said electrodes and its sheath are substantially coaxial.

6. The invention of claim 2 and further including electronic control and program means operatively associated with each of the sensor means and providing for an operation for the system for detectomg amd regulating the various levels of liquid contained within the storage tank, for providing a determination of the concentration of the solution contained therein, and for indicating when additional solution needs to be added to the storage tank to provide for the proper operation of the device.

7. The invention of claim 6 and further including means for adding additional caustic soltuion to the liquid contained within the storage tank, and said program means providing a determination as to the amount and time that additional caustic concentration needs to be added to the siad contained solution.

* * * * *

UNITED STATES PATENT AND TRADEMARK OFFICE
CERTIFICATE OF CORRECTION

PATENT NO. : 4,769,607

DATED : September 6, 1988

INVENTOR(S) : Clarence A. Bauman; Martin P. Step; and Alfred J. Gilmour

It is certified that error appears in the above—identified patent and that said Letters Patent is hereby corrected as shown below:

Column 19, line 67, change "provide" to ---provided---.

Column 20, line 5, change "and" to ---any---.

Column 20, line 35, between "second" and "probe" insert ---sensor---.

Column 22, line 9, change "siad" to ---said---.

Signed and Sealed this

Twenty-fourth Day of January, 1989

Attest:

DONALD J. QUIGG

*Attesting Officer*  *Commissioner of Patents and Trademarks*